(12) United States Patent
Hebert

(10) Patent No.: US 6,635,615 B1
(45) Date of Patent: Oct. 21, 2003

(54) STABLE SALTS OF S-ADENOSYL-L-METHIONINE

(76) Inventor: Rolland F. Hebert, 427 Belleuve Ave. E. #301, Seattle, WA (US) 98102

( * ) Notice: Subject to any disclaimer, the term of this patent is extended or adjusted under 35 U.S.C. 154(b) by 240 days.

(21) Appl. No.: 09/713,896

(22) Filed: Nov. 16, 2000

Related U.S. Application Data

(60) Provisional application No. 60/166,147, filed on Nov. 17, 1999.

(51) Int. Cl.[7] ................................................ A01N 37/18
(52) U.S. Cl. ................................ 514/2; 514/2; 514/12; 514/21; 514/46; 514/55; 536/20; 536/26.13; 536/27.3; 536/27.31; 435/88; 435/176; 435/113; 424/63
(58) Field of Search ................................ 514/2, 46, 55, 514/12, 21; 536/20, 26.13, 27.3, 27.31; 435/88, 113, 176; 424/63

(56) References Cited

U.S. PATENT DOCUMENTS

| 4,028,183 A | | 6/1977 | Fiecchi ..................... 195/28 N |
| 4,057,686 A | * | 11/1977 | Fiecchi ......................... 536/26 |
| 4,369,177 A | | 1/1983 | Kozaki ..................... 536/27.31 |
| 4,764,603 A | | 8/1988 | Zappia ......................... 536/26 |
| 4,956,173 A | * | 9/1990 | Le Fur et al. ................. 424/63 |
| 5,102,791 A | | 4/1992 | Gennari ....................... 435/113 |
| 5,998,183 A | * | 12/1999 | Le Fevre et al. ........... 435/176 |

OTHER PUBLICATIONS

McCarthy et al., Biochemistry, vol. 40, pp. 12276–12284, 2001.*

* cited by examiner

*Primary Examiner*—Christopher S. F. Low
*Assistant Examiner*—Hope A. Robinson

(57) ABSTRACT

Stable salts of S-adenosyl-1-methionine with polycations such as chitosan are described. The salts according to the invention are very stable and are valuable for use as active constituents in pharmaceutical compositions.

10 Claims, No Drawings

STABLE SALTS OF S-ADENOSYL-L-METHIONINE

BACKGROUND-CROSS-REFERENCES TO RELATED APPLICATION

This application claims the benefit of Provisional Patent Application Serial No.: 60/166,147 filed on Nov. 17, 1999.

FIELD OF THE INVENTION

The present invention relates to new salts of S-adenosyl-1-methionine.

TECHNICAL FIELD

This patent relates to new salts of S-adenosyl-1-methionine (known as SAM-e) with polycations, the processes for obtaining them and to therapeutic uses of these new salts. More particularly, the invention relates to salts deriving from the reaction between SAM-e, SAM-e salts and polycations such as chitosan, their production process, and pharmaceutical compositions that contain them as active principles.

BACKGROUND OF THE INVENTION:

SAM-e is a naturally occurring substance that is present in all living organisms and has a number of very important biological functions. SAM-e exists in two enantiomeric forms as (S,S) S-adenosyl-1-methionine and (R,S) S-adenosyl-1-methionine. Among these functions are the following:

methyl group donor in transmethylation reactions (it is the sole methyl group donor in such reactions-including methylation of DNA, proteins, hormones, catechol and indoleamines and phosphatidylethanolamine to phosphatidylcholine); it is a substrate of an enzyme lyase that converts S-adenosyl-1-methionine to the molecule methylthioadenosine and homoserine; it is an aminobutyric chain donor to tRNA; it is an aminoacidic chain donor in the biosynthesis of biotin; SAM, after decarboxylation, is the donor of aminopropyl groups for the biosynthesis of neuroregulatory polyamines spermidine and spermine. (Zappia et al (1979) Biomedical and Pharmacological roles of Adenosylmethionine and the Central Nervous System, page 1, Pergamon Press. NY.)

SAM has been used clinically for more than twenty years in the treatment of liver disease (Friedel H, Goa, K. L., and Benfield P., (1989) S-Adenosyl-1-methionine: a review of its pharmacological properties and therapeutic potential in liver dysfunction and affective disorders in relation to its physiological role in cell metabolism. Drugs. 38, 389–416), arthritis (Di Padova C, (1987) S-adenosyl-1-methionine in the treatment of osteoarthritis: review of the clinical studies. Am J. Med. 83, (Suppl. 5), 6–65), and depression (Kagan, B, Sultzer D. L., Rosenlicht N and Gerner R. (1990) Oral S-adenosylmethionine in depression: a randomized, double-blind, placebo-controlled trial. Am. J. Psychiatry 147, 591–595.) Alzheimer's patients have reduced cerebral spinal fluid levels of S-adenosyl-1-methionine (Bottiglieri et al, (1990) Cerebrospinal fluid S-adenosyl-1-methionine in depression and dementia: effects of treatment with parenteral and oral S-adenosyl-1-methionine. J. Neurol. Neurosurg. Psychiatry 53, 1096–1098.) In a preliminary study, SAM was able to produce cognitive improvement in patients with Alzheimer's disease. (Bottiglieri et al (1994) The clinical potential of admetionine (S-adenosyl-1-methionine) in neurological disorders. Drugs 48, 137–152.) SAM-e brain levels in patients with Alzheimer's disease are also severely decreased. (Morrison et al, (1996) Brain S-adenosylmethionine levels are severely decreased in Alzheimer's disease, Journal of Neurochemistry, 67, 1328–1331. Patients with Parkinson's disease have also been shown to have significantly decreased blood levels of SAM. (Cheng et al, (1997) Levels of L-methionine S-adenosyltransferase activity in erythrocytes and concentrations of S-adenosylmethionine and S-adenosylhomocysteine in whole blood of patients with Parkinson's disease. Experimental Neurology 145, 580–585.) Oral SAM-e administration to patients with and without liver disease has resulted in increases in liver glutathione levels. (Vendemiale G et al, Effect of oral S-adenosyl-1-methionine on hepatic glutathione in patients with liver disease. Scand J Gastroenterol 1989;24:407–15. Oral administration of SAM-e to patients with suffering from intaahepatic cholestasis had improvements in both the pruritus as well as the biochemical markers of cholestasis. (Giudici et al, The use of admetionine (SAM-e) in the treatment of cholestatic liver disorders. Meta-analysis of clinical trials. In: Mato et al editors. Methionine Metabolism: Molecular Mechanism and Clinical Implications. Madrid: CSIC Press; 1992 pp 67–79.) Oral SAM-e administration to patients suffering from primary fibromyalgia resulted in significant improvement after a short term trial. (Tavoni et al, Evaluation of S-adenosylmethionine in Primary Fibromyalgia. The American Journal of Medicine, Vol 83 (suppl 5A), pp 107–110, 1987.)

SAM-e is clinically useful in many apparently unrelated areas because of its important function in basic metabolic processes. One of its most string clinical uses is in the treatment of alcoholic liver cirrhosis that, until now, remained medically untreatable. Mato et al, in 1999, demonstrated the ability of oral SAM in alcoholic liver cirrhosis to decrease the overall mortality and/or progression to liver transplant by 29% vs 12% as compared with a placebo treated group. (Mato et al, (1999) S-adenosylmethionine in alcohol liver cirrhosis: a randomized, placebo-controlled, double blind, multi-center clinical trial, Journal of Hepatology, 30, 1081–1089.) The extensive clinical use of SAM-e has proven its efficacy as well as its absence of toxicity in a number of different clinical conditions. Indeed, further basic science as well as clinical studies on this very important molecule may elucidate new uses for SAM-e in medicine.

SAM-e, however, presents certain difficult problems in terms of its stability at ambient temperature that result in degradation of the molecule to undesirable degradation products. SAM-e has therefore been the subject of numerous patents directed both towards the obtaining of new stable salts, and towards the provision of preparation processes which can be implemented on an industrial scale. There exist numerous patents disclosing many new salts of SAM-e but none discloses polycation salts such as chitosan salts of SAM-e. The following are representative patents of SAM-e salts currently on the pharmaceutical marketplace: Gennari, U.S. Pat. No. 5,102,791 Apr. 7, 1992, discloses, among others, a 1,4 butanedisulfonate salt of SAM-e but not polycation salts such as chitosan salts of SAM-e or of other SAM-e salts. Fiecchi, U.S. Pat. No. 4,028,183, Jun. 7, 1977, discloses, among others, p-toluene sulfonate as a means to stabilize the SAM-e molecule but does not disclose polycation salts such as chitosan salts of SAM-e or a salt of SAM-e. Kozaki et al, U.S. Pat. No. 4369177, Jan. 18, 1983, discloses stable compositions of SAM-e and SAM-e salts using a salt of a bivalent or trivalent metal but does not disclose the use of polycation salts such as chitosan salts of SAM-e or a salt of SAM-e. Zappia, U.S. Pat. No. 4764603, Aug. 16, 1988, discloses the use of polyanions such as polyphosphates, polyvinylsulfonates-sulfates or phosphates, polyacrylates, and polystyrene sulfonates. However, this patent does not disclose the use of a polycation salts such as chitosan salts of SAM-e or of SAM-e salts.

Administration of new SAM-e salts of the present invention would have significant utility over a wide range of disorders or conditions associated with low levels of SAM-e. These new salts would not cause gastrointestinal upset often associated with the current SAM-e salts. In this regard, and in view of the molecular instability of SAM-e at room temperature over time, it has been suggested that a more ideal salt of SAM-e would be able to withstand the conditions of room temperature over long periods of time which would duplicate the shelf life conditions under which these new SAM-e salts would be stored.

Accordingly, there is need in the art for new, stable salts of SAM-e as well as methods related to the use of such salts to increase blood and other tissue and fluid levels of SAM-e and to treat conditions which result from low blood and tissue levels of SAM-e. There is also a need in the art for synthetic routes to make such new salts. The author of this present invention fulfills these needs and provides further related advantages.

SUMMARY OF THE INVENTION

Briefly stated, the present invention discloses new, stable salts of SAM-e, methods for the use thereof and synthetic methods for their preparation. These new salts of SAM-e of this present invention have utility in increasing blood and other tissue or fluid levels of SAM-e, as well as treating or preventing a wide variety of conditions associated with low blood or other tissue or fluid levels of SAM-e. Thus in one embodiment, a new SAM-e salt is administered to a warm-blooded animal in need thereof to increase SAM-e levels. In another embodiment, a new SAM-e salt is administered to a warm blooded animal in need thereof to prevent or treat a condition associated with low levels of SAM-e. In yet a further embodiment, a new SAM-e salt is administered to a warm blooded animal in need thereof to prevent and or treat the following conditions: aging, aging of the skin, Alzheimer's disease, arthritis, both as an anti-inflammatory as well as to promote new cartilage formation, nerve damage associated with HIV/AIDS, anxiety, obsessive compulsive disorder, attention deficit disorder and ADHD, sleep regulation, organ preservation for transplant industry, treatment of dyslipidemias, excess sebum production, migraines, prevention and treatment of bile dysfunction caused by pregnancy and use of contraceptive medications, cancer, depression, acute and chronic liver disease, cirrhosis of the liver, ischemic reperfusion injury of stroke as well as organ ischemic reperfusion in transplant technology, Parkinson's disease, memory disturbances, intrahepatic cholestasis, inflammation, pain and to counteract the decrease in SAM-e caused by various cancer drugs.

DETAILED DESCRIPTION OF THE INVENTION

As mentioned above, this invention is generally directed to new salts of SAM-e. Such new SAM-e salts when administered to a warm blooded animal in need thereof have utility in the prevention or treatment of conditions associated with low levels of SAM-e in warm blooded animals, including humans.

As used herein, the term "conditions" includes diseases, injuries, disorders, indications and/or afflictions that are associated with decreased levels of SAM-e. The term "treat" or "treatment" means that the symptoms associated with one or more conditions associated with low levels of SAM-e are alleviated or reduced in severity or frequency and the term "prevent" means that subsequent occurrences of such symptoms are avoided or that the frequency between such occurrences is prolonged.

The following examples illustrate the synthetic process by which the new stabilized salts may be made. These examples are given to illustrate the present invention, but not by way of limitation. Accordingly, the scope of this invention should be determined not by the embodiments illustrated, but rather by the appended claims and their legal equivalents.

EXAMPLE 1

Chitosan (a polyglucosamine) (38.9 mg, degree of deacetylation 83.6%) was added to S-adenosylmethionine chloride (200 mg) in 5 ml deionized water. The solution was stirred for 4 hours, filtered and freeze dried.

EXAMPLE 2

Chitosan (a polyglucosamine) (30.5 mg, degree of deacetylation 83.6%) was added to S-adenosylmethionine sulfate p-toluenesulfonate (200 mg) in 5 ml deionized water. The solution was stirred for 4 hours, filtered and freeze dried.

EXAMPLE 3

Chitosan (a polyglucosamine) (38.9 mg, degree of deacetylation 83.6%) was added to S-adenosylmethionine chloride (200 mg) in 5 ml deionized water. The solution was stirred under nitrogen for 4 hours, filtered and freeze dried.

EXAMPLE 4

Chitosan (a polyglucosamine) (30.5 mg, degree of deacetylation 83.6%) was added to S-adenosylmethionine sulfate p-toluenesulfonate (200 mg) in 5 ml deionized water. The solution was stirred under nitrogen for 4 hours, filtered and freeze dried.

EXAMPLE 5

Chitosan (a polyglucosamine) (15.25 mg, degree of deacetylation 80.1%) was added to S-adenosylmethionine chloride (200 mg) in 5 ml deionized water. The solution was stirred for 4 hours, filtered and freeze dried.

EXAMPLE 6

Chitosan (a polyglucosamine) (39.5 mg, degree of deacetylation 80.1%) was added to S-adenosylmethionine chloride (200 mg) in 5 ml deionized water. The solution was stirred for 4 hours, filtered and freeze dried.

EXAMPLE 7

Chitosan (a polyglucosamine) (39.5 mg, degree of deacetylation 80.1%) was added to S-adenosylmethionine chloride (200 mg) in 5 ml deionized water. The solution was stirred under nitrogen for 4 hours, filtered and freeze dried.

EXAMPLE 8

Chitosan (a polyglucosamine) (39.5 mg, degree of deacetylation 80.1%) was added to S-adenosylmethionine chloride (200 mg) in 5 ml deionized water. The solution was stirred in an ice bath for 6 hours, filtered and freeze dried.

EXAMPLE 9

Chitosan (a polyglucosamine) (39.5 mg, degree of deacetylation 80.1%) was added to S-adenosylmethionine chloride (200 mg) in 5 ml deionized water. The solution was stirred under nitrogen for 4 hours, filtered and freeze dried.

S-adenosylmethionine chloride, S-adenosylmethionine sulfate-p-toluenesulfonate and chitosan are available commercially from Sigma Chemical Company, St. Louis, Mo.

EXAMPLE 10

| compound | Analysis:<br>May 11, 2000<br>Concentration<br>1:500 (nmol/L) | Analysis:<br>Aug. 22, 2000<br>Concentration<br>1:500 (nmol/L) | % Change |
|---|---|---|---|
| SAM-e-1,4-butane-disulphonate | 1417.96 | 794.41 | −43.9% |
| Chitosan salt of SAMe-1,4-butane-disulphonate | 617.31 | 536.22 | −13.1% |

SAM-e-1, 4-butane-disulphonate and chitosan salt of SAM-e 1, 4-butane-disulphonate were stored at room temperature, in a closed, clear glass vial at constant humidity. HPLC analysis done according to Bottligleri, T. (1990) Isocratic high performance liquid chromatographic analysis of S-adenosylmethionine and S-adenosylhomocysteine in animal tissues: the effect of exposure to nitrous oxide. Biomed Chromatogr, 4(6):239–41. The SAM-e 1,4 butane-disulphonate deteriorated by 43% over the period of time. By contrast, however, chitosan salt of SAM-e 1, 4-butane-disulphonate deteriorated by only 13.1% over the same period.

EXAMPLE 11

Stability study-of polycation (chitosan) salt of SAM-e tosylate

| compound | Analysis:<br>Dec. 28, 1999<br>Concentration<br>0.5 mg/ml<br>1:125 (nmol/L) | Analysis:<br>Apr. 4, 2000<br>Concentration<br>0.5 mg/ml<br>1:125 (nmol/L) | % Change |
|---|---|---|---|
| SAM-e tosylate | 3492 | 247.9 | −92.9.0% |
| Chitosan salt of SAM-e tosylate | 3687 | 3280 | −11.04% |

SAM-e tosylate and chitosan salt of SAM-e tosylate were stored at room temperature, in a closed, clear glass vial at constant humidity. HPLC analysis done according to Bottligleri, T. (1990) Isocratic high performance liquid chromatographic analysis of S-adenosylmethionine and S-adenosylhomocysteine in animal tissues: the effect of exposure to nitrous oxide. Biomed Chromatogr, 4(6):239–41. The SAM-e tosylate deteriorated by 92.9% over the period of time. By contrast, however, chitosan salt of SAM-e tosylate deteriorated by only 11.04% over the same period.

As can be seen from examples 10 and 11, the new chitosan salts of SAM-e are much more stable at room temperature than salts of SAM-e which are currently pharmaceutically available.

I claim:

1. A composition comprising S-adenosyl-1-methionine salts and a chitosan.

2. A composition of claim 1 where chitosan is present from 1% to 90%.

3. A composition of claim 1 where chitosan is present from 20% to 50%.

4. A composition of claim 1 wherein S-adenosyl-1-methionine salt is selected from the group consisting of S-adenosyl-1-methionine tosylate bisulfate, S-adenosyl-1-methionine-1,4-butanedisulfonate, S-adenosyl-1-methionine sulfate, and S-adenosyl-1-methionine tosylate.

5. A composition of claim 1 wherein S-adenosyl-1-methionine salt is selected from the group consisting of S-adenosyl-1-methionine bisulfate, S-adenosyl-1-methionine tri-p-toluene-sulfonate, S-adenosyl-1-methionine di-p-toluenesulfonate, S-adenosyl-1-methionine di-p-toluenesulfonate, S-adenosyl-1-methionine disulfate, S-adenosyl-1-methionine chloride, S-adenosyl-1-methionine carbonate, S-adenosyl-1-methionine bicarbonate, S-adenosyl-1-methionine bromide, S-adenosyl-1-methionine iodide, and S-adenosyl-1-methionine hydrochloride.

6. A composition of claim 1 wherein S-adenosyl-1-methionine, salt sulphonic acids selected from the group consisting of methanesulphonic, ethanesulphonic, 1-n-dodecanesulphonic, 1-n-octadecanesulphonic, 2-chloroethanesulphonic, 2-bromoethanesulphonic, 2-hydroxyethanesulphonic, 3-hydroxypropanesulphonic, d-,1-,d,-1-10-camphorsulphonic, d-,1-,d,1-3-bromocamphor-10-sulphonic, cysteic, benzenesulphonic,p-chlorobenzenesulphonic, 2-mesitylbenzenesulphonic, 4-biphenylsulphonic, 1-naphthalenesulphonic, 2-naphthalenesulphonic, 5-sulphosalicylic, p-acetylbenzenesulphonic, 1,2-ethanedisulphonic, methanesulphonic acid, ethanesulphonic acid, 1-n-dodecanesulphonic acid, 1-n-octadecanesulphonic acid, 2-chloroethanesulphonic acid, 2-bromoethanesulphonic acid, 2-hydroxyethanesulphonic acid, d-,1-,d,1–10-camphorsulphonic acid, d-,1-,d,1–3-bromocamphor-10-sulphonic acid, cysteic acid, benzenesulphonic acid, 3-hydroxypropanesulphonic acid, 2-mesitylbenzenesulphonic acid,p-chlorobenzenesulphonic acid, 4-biphenylsulphonic acid, 2-naphthalenesulphonic acid, 5-sulphosalicylic acid, 1,2-ethanedisulphonic acid, p-acetylbenzenesulphonic acid, 1-naphthalenesulphonic acid, o-benzenedisulphonic and chondroitinesulphuric acids, and double salts of said acids with sulphuric acid.

7. A composition of claim 1 where S-adenosyl-1-methionine is selected from the group consisting of: S-adenosyl-L-methionine lithium chloride, S-adenosyl-L-methionine lithium bromide, S-adenosyl-L-methionine lithium iodide, S-adenosyl-L-methionine lithium sulfate, S-adenosyl-L-methionine lithium nitrate, S-adenosyl-L-methionine lithium phosphate, S-adenosyl-L-methionine lithium borate, S-adenosyl-L-methionine lithium carbonate, S-adenosyl-L-methionine lithium formate, S-adenosyl-L-methionine lithium acetate, S-adenosyl-L-methionine lithium citrate, S-adenosyl-L-methionine lithium succinate and lithium benzoate.

8. A composition of claim 1 wherein S-adenosyl-1-methionine salt is selected from the group consisting of the optically pure diasteriomer (S,S) S-adenosyl-1-methionine or a defined ratio non-racemic ratio of (S,S) S-adenosyl-1-methionine and (R,S) S-adenosyl-1-methionine.

9. A composition of claim 8 wherein the defined non-racemic ratio of (S,S) S-adenosyl-1-methionine: (R,S) S-adenosyl-1-methionine is about 1%:100% to about 100%:1% by weight.

10. A composition according to claim 1 for the treatment of a condition in warm-blooded animals that responds to increasing tissue and blood levels of S-adenosyl-1-methionine.

\* \* \* \* \*